US011685950B2

(12) United States Patent
Lee et al.

(10) Patent No.: US 11,685,950 B2
(45) Date of Patent: Jun. 27, 2023

(54) METHOD OF DIAGNOSING AND TREATING ACUTE REJECTION IN KIDNEY TRANSPLANT PATIENTS

(71) Applicant: University-Industry Cooperation Group of Kyung Hee University, Gyeonggi-do (KR)

(72) Inventors: Sangho Lee, Seoul (KR); Jungwoo Seo, Seoul (KR)

(73) Assignee: University-Industry Cooperation Group of Kyung Hee University, Gyeonggi-do (KR)

( * ) Notice: Subject to any disclaimer, the term of this patent is extended or adjusted under 35 U.S.C. 154(b) by 474 days.

(21) Appl. No.: 16/727,281

(22) Filed: Dec. 26, 2019

(65) Prior Publication Data
US 2020/0232031 A1    Jul. 23, 2020

(30) Foreign Application Priority Data

Dec. 26, 2018  (KR) .................. 10-2018-0169490

(51) Int. Cl.
| | | |
|---|---|---|
| C12Q 1/6876 | (2018.01) | |
| C12Q 1/6883 | (2018.01) | |
| G06F 17/18 | (2006.01) | |
| G16B 25/10 | (2019.01) | |
| A61K 45/06 | (2006.01) | |

(52) U.S. Cl.
CPC ........... *C12Q 1/6876* (2013.01); *G06F 17/18* (2013.01); *G16B 25/10* (2019.02); *A61K 45/06* (2013.01); *C12Q 1/6883* (2013.01); *C12Q 2600/158* (2013.01); *C12Q 2600/178* (2013.01); *G01N 2800/245* (2013.01); *G01N 2800/52* (2013.01)

(58) Field of Classification Search
None
See application file for complete search history.

(56) References Cited

U.S. PATENT DOCUMENTS

| | | |
|---|---|---|
| 9,936,579 B2 | 4/2018 | Akre et al. |
| 9,982,301 B2 | 5/2018 | Muthukumar et al. |
| 2014/0213533 A1 | 7/2014 | Suthanthiran et al. |

OTHER PUBLICATIONS

Wolenski (Journal of Applied Toxicology 2017; 37:278-286).*
Cho (Nephrology Dialysis Transplantation vol. 33 Issue Suppl_1 May 2018 p. i281).*
Gielis (Nephrology Dialysis Transplantation vol. 32 Issue Suppl_3 May 2017 p. iii724).*
Vahed (Int Urol Nephrol (2017) 49:1681-1689).*
Anglicheau et al. "MicroRNA Expression Profiles Predictive of Human Renal Allograft Status" PNAS vol. 106, pp. 5330-5335, 2009.
Janszky et al. "Circulating and Urinary MicroRNAs as Possible Biomarkers in Kidney Transplantation" Transplantation Reviews vol. 32, pp. 110-118, 2017.
Millan et al. "Urinary MiR-155-5p and CXCL10 as Prognostic and Predictive Biomarkers of Rejection, Graft Outcome and Treatment Response in Kidney Transplantation" British Journal of Clinical Pharmacology vol. 83, pp. 2636-2650, 2017.
Bijkerk et al. "Acute Rejection After Kidney Transplantation Associates with Circulating MicroRNAs and Vascular Injury" Transplantation Direct vol. 3, pp. 1-9, 2017.
Iwasaki et al. "MIR-142-5p and miR-486-5p as Biomarkers for Early Detection of Chronic Antibody-Mediated Rejection in Kidney Transplantation" Biomarkers vol. 22, pp. 45-54, 2017.
Kotton et al. "The Third International Consensus Guidelines on the Management of Cytomegalovirus in Solid-Organ Transplantation" Transplantation vol. 102, pp. 900-931, 2018.
Liu et al. "MicroRNA-10b Downregulation Mediates Acute Rejection of Renal Allografts by Derepressing BCL2L11" Experimental Cell Research vol. 333, pp. 155-163, 2015.
Ong et al "Genomic and Proteomic Fingerprints of Acute Rejection in Peripheral Blood and Urine" Transplantation Reviews vol. 29, pp. 60-67, 2015.
Seo et al "Both Absolute and Relative Quantification of Urinary mRNA are Useful for Non-Invasive Diagnosis of Acute Kidney Allograft Rejection" PLoS ONE vol. 12, pp. 1-13, 2017.

(Continued)

*Primary Examiner* — Amanda Haney
(74) *Attorney, Agent, or Firm* — Cesari & McKenna, LLP

(57) ABSTRACT

Provided are a method of diagnosing the onset of acute rejection, the method including the step of correlating expression levels of one or more miRNAs selected from the group consisting of 8 kinds of miRNAs including miR-4488, miR-4532, miR-146a-5p, miR-21-5p, miR-373-3p, miR-31-5p, miR-223-3p, and miR-210-3p, and a combination thereof with the onset of acute rejection in kidney transplant patients, a composition for diagnosing acute rejection, the composition including an agent capable of measuring the expression level of each of the miRNAs, a kit for diagnosing acute rejection, the kit including the composition, and a method of treating acute rejection, the method including the step of treating acute rejection, when the onset of acute rejection is identified by the above diagnostic method. Since miR-4488, miR-4532, miR-146a-5p, miR-21-5p, miR-373-3p, miR-31-5p, miR-223-3p, and miR-210-3p according to the present invention exist in high levels in the urine of a patient with acute kidney transplant rejection, they may be used to easily diagnose the onset of acute kidney transplant rejection, thereby being used in the effective treatment of acute rejection after kidney transplantation.

6 Claims, 7 Drawing Sheets

(56) References Cited

OTHER PUBLICATIONS

Sui et al. "Microarray Analysis of MicroRNA Expression in Acute Rejection After Renal Transplantation" Transplant Immunology vol. 19, pp. 81-85, 2008.
Wilflingseder et al. "miRNA Profiling Discriminates Types of Rejection and Injury in Human Renal Allografts" Transplantation vol. 95, pp. 835-841, 2013.

* cited by examiner

[Fig. 1A]
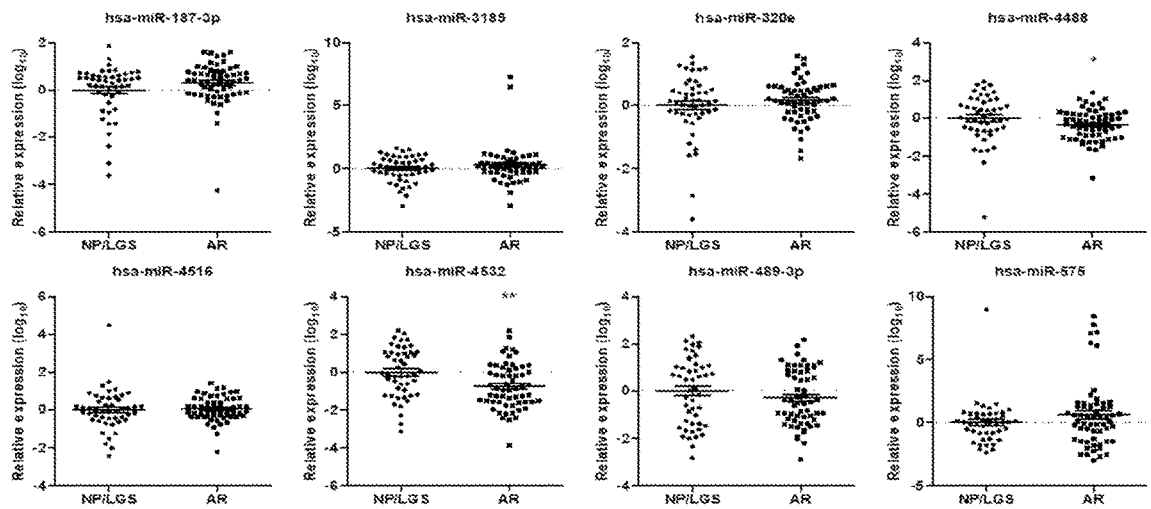
[Fig. 1B]
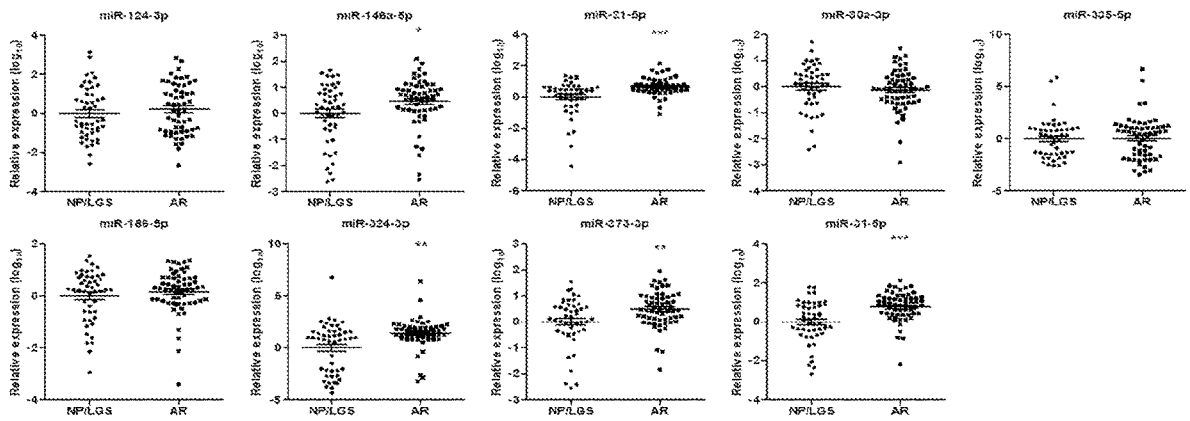

[Fig. 1C]
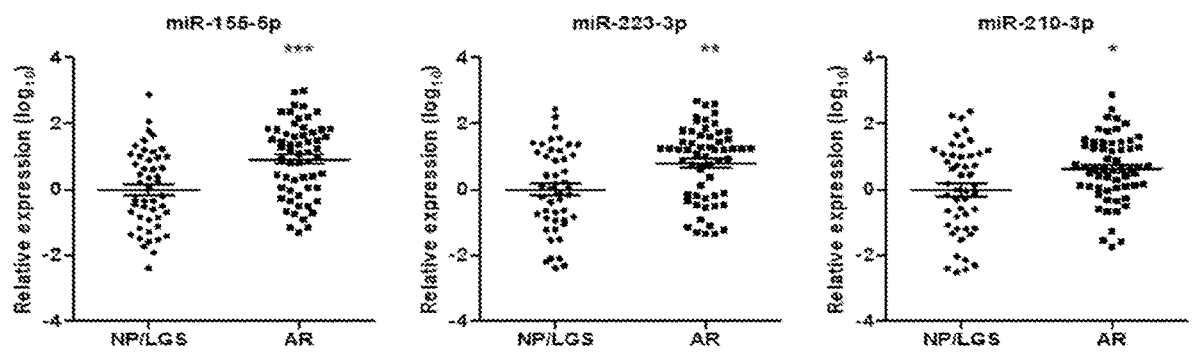

[Fig. 2]
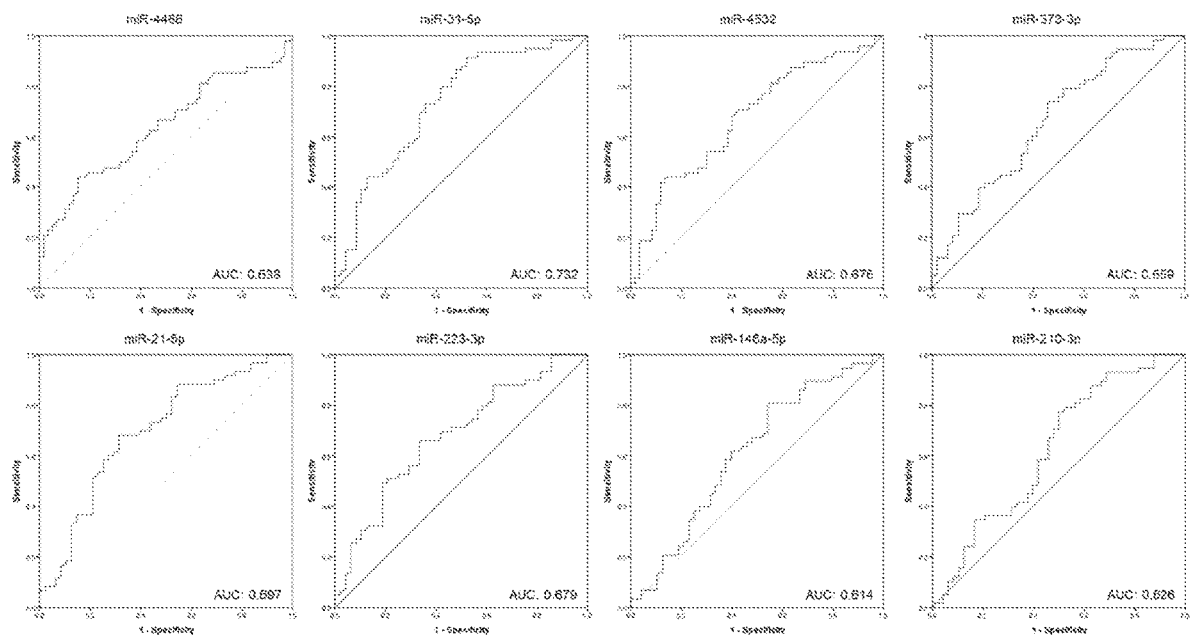

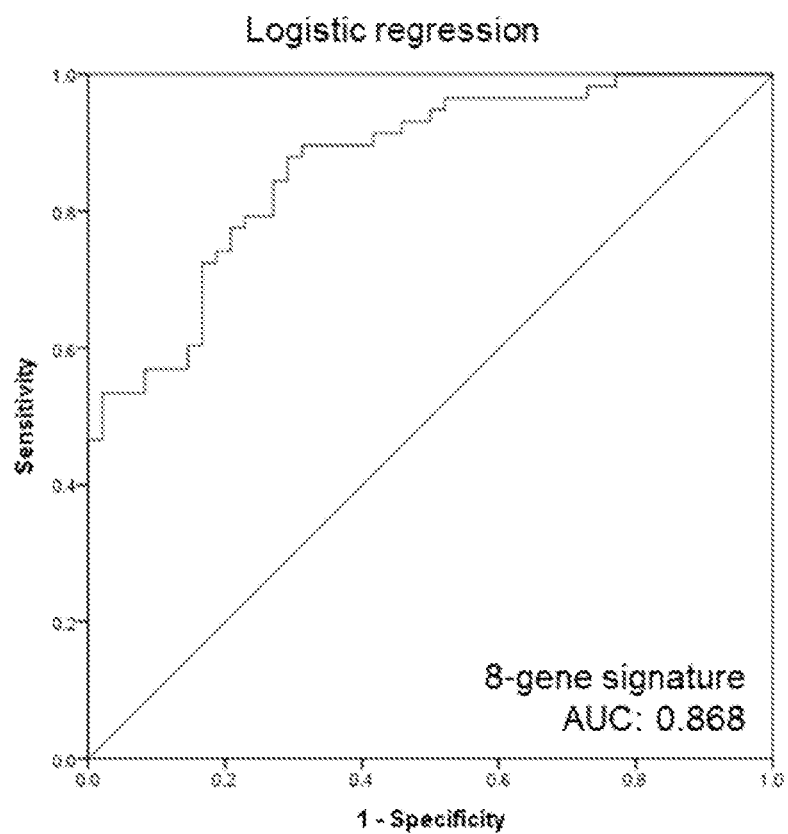

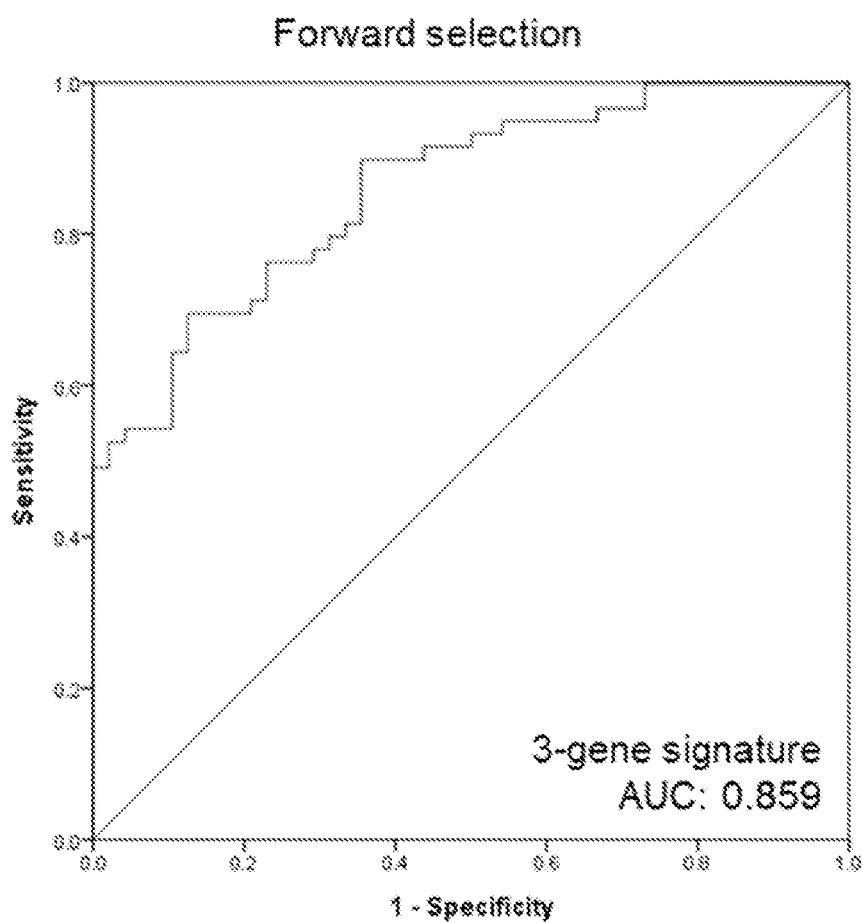
[Fig. 3B]

[Fig. 4A]
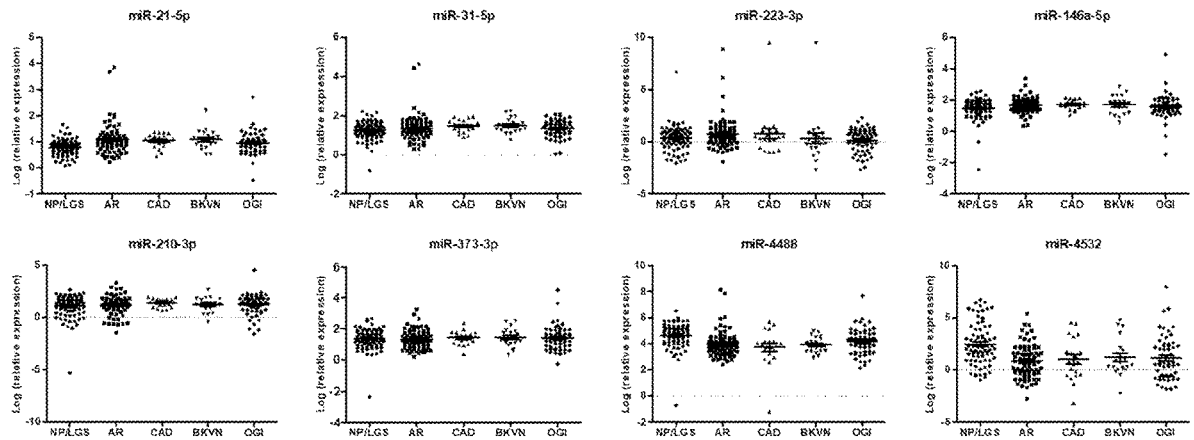
[Fig. 4B]
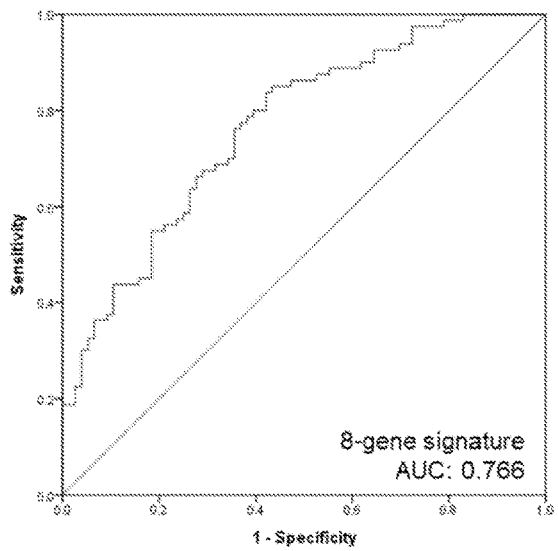

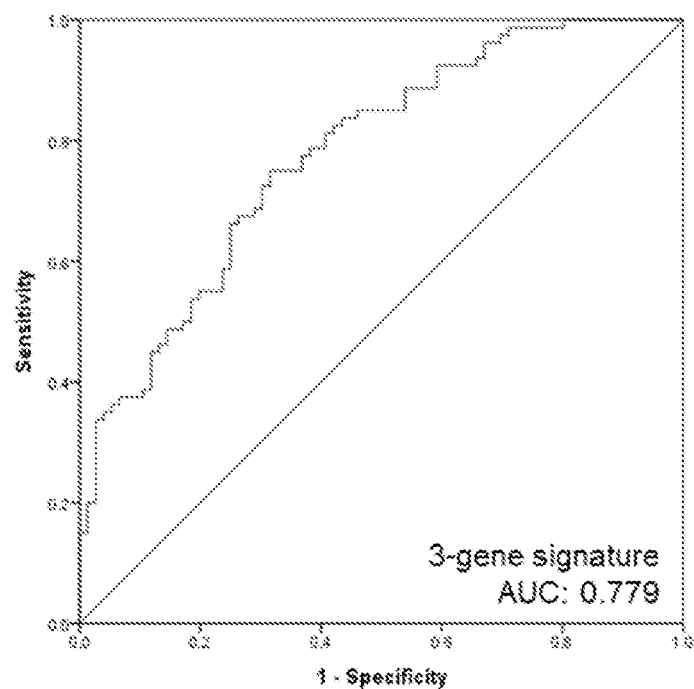
[Fig. 4C]

METHOD OF DIAGNOSING AND TREATING ACUTE REJECTION IN KIDNEY TRANSPLANT PATIENTS

CROSS-REFERENCE TO RELATED APPLICATION

This application claims the benefit of priority of Korean Application No. 10-2018-0169490, filed Dec. 26, 2018, the content of it being hereby incorporated by reference in its entirety for all purposes.

BACKGROUND OF THE INVENTION

1. Field of the Invention

The present invention relates to a method of diagnosing and treating acute rejection in kidney transplant patients. Particularly, the present invention relates to a method of diagnosing the onset of acute rejection, the method including the step of correlating expression levels of one or more miRNAs selected from the group consisting of 8 kinds of miRNAs including miR-4488, miR-4532, miR-146a-5p, miR-21-5p, miR-373-3p, miR-31-5p, miR-223-3p, and miR-210-3p, and a combination thereof with the onset of acute rejection in kidney transplant patients, a composition for diagnosing acute rejection, the composition including an agent capable of measuring the expression level of each of the miRNAs, a kit for diagnosing acute rejection, the kit including the composition, and a method of treating acute rejection, the method including the step of treating acute rejection, when the onset of acute rejection is identified by the above diagnostic method.

2. Description of the Related Art

The human body's immune system functions to destroy protein components that invade the human body to cause diseases, such as bacteria, viruses, etc. However, the immune system cannot distinguish foreign proteins such as bacteria or viruses from transplanted kidney tissues, and recognizes the transplanted kidney as an external invader to attack it. A process by which the immune system attacks the transplanted kidney is called kidney transplant rejection.

Acute rejection after kidney transplantation is generally asymptomatic, but if left untreated, it may involve loss of function of the transplanted kidney. Early after transplantation, uremic symptoms may result from decreased kidney functions, such as loss of appetite, decreased urine output, swelling, difficulty breathing, etc. Therefore, when acute rejection is suspected after transplantation, diagnosis through biopsy and treatment are recommended. However, the biopsy of directly collecting tissues has a disadvantage of increasing the burden on the patient in terms of cost, time, or recovery, and also has a problem that it is difficult to improve the diagnostic time of tissue biopsy, because it takes 2-3 days.

Accordingly, various methods of easily diagnosing acute kidney transplant rejection have been developed. For example, a method of diagnosing kidney allograft rejection by comparing expression levels of specific genes in the blood has been developed (U.S. Pat. No. 9,936,579B2). However, since the above method also involves the inconvenience of blood collection, development of a non-invasive method that overcomes the cumbersome process such as blood collection has been required.

Meanwhile, apart from the method of diagnosing rejection using blood mRNA, various researchers have attempted to diagnose or predict rejection in kidney transplant patients by measuring urinary mRNAs (US 20140213533, U.S. Pat. No. 9,982,301). However, since the diagnostic technology to use urinary mRNAs has a detection limitation due to mRNA instability and a difficulty in quantification due to limitation of mRNA which is an unstable nucleic acid in the urine environment, development of a more stable method of diagnosing the rejection using urinary nucleic acids is also required.

Under this background, the present inventors have made intensive efforts to develop a method of diagnosing acute rejection in a kidney transplant patient in a non-invasive manner, based on that urinary miRNA is stable in an exome fraction and urinary miRNA may reflect disease conditions, and as a result, they found that the onset of acute rejection of the kidney transplant patient in need of treatment may be diagnosed, predicted, and treated using miRNA derived from the urinary exosome of the patient, thereby completing the present invention.

SUMMARY OF THE INVENTION

An object of the present invention is to provide a method of diagnosing the onset of acute rejection, the method including the steps of measuring expression levels of one or more miRNAs selected from the group consisting of 8 kinds of miRNAs including miR-4488, miR-4532, miR-146a-5p, miR-21-5p, miR-373-3p, miR-31-5p, miR-223-3p, and miR-210-3p, and a combination thereof, and correlating the expression levels with the onset of acute rejection in kidney transplant patients.

Another object of the present invention is to provide a composition for diagnosing acute rejection, the composition including an agent capable of measuring the expression level of each of the miRNAs.

Still another object of the present invention is to provide a kit for diagnosing acute rejection, the kit including the composition.

Still another object of the present invention is to provide a method of treating acute rejection, the method including the step of treating acute rejection, when the onset of acute rejection is identified by the method of diagnosing the onset of acute rejection.

BRIEF DESCRIPTION OF THE DRAWINGS

FIG. 1A shows graphs of the results of real-time PCR system for analyzing 8 biomarker candidates, except for undetected 3 biomarker candidates, among 11 biomarker candidates identified using a Nanostring nCounter system;

FIG. 1B shows graphs of the results of real-time PCR system for analyzing 9 biomarker candidates, except for undetected 1 biomarker candidate, among 10 biomarker candidates identified using bioinformatics techniques;

FIG. 1C shows graphs of the results of real-time PCR system for analyzing 3 biomarker candidates, except for undetected 2 biomarker candidate, among 5 biomarker candidates identified through literature review;

FIG. 2 shows graphs of the results of analyzing ROC curves of 8 kinds of miRNAs (miR-4488, miR-4532, miR-146a-5p, miR-21-5p, miR-373-3p, miR-31-5p, miR-223-3p, and miR-210-3p);

FIG. 3A shows a graph of the results of predicting rejection in 108 samples for biomarker development using a first model;

FIG. 3B shows a graph of the results of predicting rejection in 108 samples for biomarker development using a second model;

FIG. 4A shows graphs of the results of real-time PCR system for analyzing 8 kinds of miRNAs identified in Example 4 in 260 samples for biomarker validation;

FIG. 4B shows a graph of the results of predicting rejection in 260 samples for biomarker validation using the first model; and FIG. 4C shows a graph of the results of predicting rejection in 260 samples for biomarker validation using the second model.

DETAILED DESCRIPTION OF THE PREFERRED EMBODIMENTS

To achieve the above-described objects, an aspect of the present invention provides a method of diagnosing the onset of acute rejection in a kidney transplant patient.

Specifically, the method of diagnosing the onset of acute rejection in a kidney transplant patient of the present invention includes the steps of:

(a) obtaining a sample isolated from an individual suspected of developing acute kidney transplant rejection;

(b) quantitatively analyzing expression levels of one or more miRNAs selected from the group consisting of miR-4488, miR-4532, miR-146a-5p, miR-21-5p, miR-373-3p, miR-31-5p, miR-223-3p, miR-210-3p, and a combination thereof in the obtained sample, and (c) correlating the quantitatively analyzed miRNA expression levels with the onset of acute kidney transplant rejection to predict or identify the onset of acute kidney transplant rejection.

Hereinafter, the step (a) will be described in detail.

As used herein, the term "acute kidney transplant rejection" refers to a type of rejection that occurs in an individual who has received a kidney transplant.

As used herein, the term "rejection" refers to a series of reactions that inhibit the function of the transplanted kidney tissue by the immune response of an individual who has received a kidney transplant. The rejection results in loss of function of the transplanted kidney tissue. The main symptoms of the rejection may include high fever, body aches, colds, pain or tenderness of the graft site, abnormal weight gain or swelling, a decrease in urine output, and the like.

The rejection may be classified into hyperacute rejection, acute rejection, and chronic rejection according to the time of occurrence. Among them, hyperacute rejection refers to rejection occurring during transplantation or within a few hours after transplantation. Acute rejection refers to rejection occurring within 5 days to 6 months after transplantation. Chronic rejection occurs at 6 months after transplantation.

As used herein, the term "individual" may include, without limitation, mammals including rats, livestock, humans, etc., farmed fish, etc., which are suspected of having or already have acute kidney transplant rejection.

Hereinafter, the step (b) will be described in detail.

The present inventors collected urine samples from patients with graft biopsy after kidney transplantation, and divided the samples into samples for biomarker development and samples for biomarker validation. The samples for biomarker development were used to identify 8 kinds of miRNA-type biomarkers for diagnosing/predicting rejection (miR-4488, miR-4532, miR-146a-5p, miR-21-5p, miR-373-3p, miR-31-5p, miR-223-3p, and miR-210-3p).

Furthermore, the present inventors developed two kinds of diagnostic/predictive models for rejection using the biomarkers, and they found that the developed two kinds of diagnostic/predictive models for rejection may be used to predict the onset of rejection in samples for biomarker validation.

Accordingly, it could be seen that the 8 kinds of miRNAs may be used as markers for diagnosing or predicting kidney transplant rejection.

A method of quantitatively analyzing an expression level of each of the identified miRNAs may be any method known to those skilled in the art. Specific examples thereof may include PCR, ligase chain reaction (LCR), transcription amplification, self-sustained sequence replication, nucleic acid sequence-based amplification (NASBA), etc., but are not limited thereto. In this regard, since nucleotide sequences of the 8 kinds of miRNAs according to the present invention are disclosed in the database, such as NCBI, etc., those skilled in the art may employ an appropriate means required for measuring the miRNA expression levels.

Hereinafter, the step (c) will be described in detail.

A method of correlating the quantitatively analyzed miRNA expression levels with the onset of acute kidney transplant rejection may be carried out by combination of the results of quantitatively analyzing the miRNA expression levels.

In other words, since each of the miRNAs is also detected in the urine of a normal person or a kidney transplant patient with stable prognosis, it may not be easy to diagnose acute kidney transplant rejection by simply using each of the miRNAs levels. Therefore, by analyzing the miRNA expression levels in combination, it is possible to more accurately diagnose acute kidney transplant rejection.

A method of analyzing the quantitatively analyzed miRNA expression levels in combination, as described, may be carried out by a common statistical analysis method. In this regard, the applicable statistical analysis method is not particularly limited, as long as it is able to diagnose acute kidney transplant rejection. For example, linear or nonlinear regression methods (Lasso penalized logistic regression, Forward stepwise selection, Logistic regression, forward stepwise selection, etc.); linear or nonlinear classification methods; analysis of variance (ANOVA) methods; neural network methods; genetic analysis methods; support vector machine analysis methods; hierarchical analysis or clustering analysis methods; hierarchical algorithms using decision trees, or kernel principal components analysis methods; Markov Blanket analysis methods; RFE (recursive feature elimination) analysis methods; forward or backward FS (floating search) analysis methods may be used alone or in combination.

Further, the combination of the detection results may be carried out using a computer algorithm capable of automatically perform the statistical methods.

A specific example of the combination of the detection results may be a regression model of the following [Equation 1], which is obtained by linear or nonlinear regression analysis of the total expression levels of the 8 kinds of miRNAs:

i) $\ln\left(\dfrac{p}{1-p}\right) =$ [Equation 1]

$-1.284 + (0.267 \times miR4488) + (-1.361 \times miR4532) +$ $(1.544 \times miR21) + (0.015 \times miR223) + (1 \times miR31) +$ $(-0.497 \times miR146a) + (0.3 \times miR373) + (0.146 \times miR210)$ in Equation,
miR4488 represents an expression level of miR-4488,
miR4532 represents an expression level of miR-4532,
miR21 represents an expression level of miR-421-5p,
miR223 represents an expression level of miR-223-3p,
miR31 represents an expression level of miR-31-5p,
miR146a represents an expression level of miR-146a-5p,
miR373 represents an expression level of miR-373-3p, and
miR210 represents an expression level of miR-213-3p.

A cutoff value of the regression model of [Equation 1] is 0.572. If a result obtained by applying the expression levels of the 8 kinds of miRNAs to Equation 1 is higher than 0.572, it may be predicted that acute rejection will be diagnosed after graft biopsy. If the result is lower than 0.572, it may be predicted that acute rejection will not be diagnosed after graft biopsy.

Another specific example of the combination of the detection results may be a regression model of the following [Equation 2], which is obtained by linear or nonlinear regression analysis of the expression levels of three kinds of miRNAs (miR-21-5p, miR-31-5p, and miR-4532):

$$\text{ii}) \ln\left(\frac{p}{1-p}\right) = -1.158 + \quad \text{[Equation 2]}$$
$$(-1.103 \times miR4532) + (1.2 \times miR21) + (1.16 \times miR31)$$

in Equation,
miR4532 represents an expression level of miR-4532,
miR21 represents an expression level of miR-21-5p, and
miR31 represents an expression level of miR-31-5p.

A cutoff value of the regression model of [Equation 2] is 0.650. If a result obtained by applying the expression levels of the three kinds of miRNAs (miR-21-5p, miR-31-5p, and miR-4532) to Equation 2 is higher than 0.650, it may be predicted that acute rejection will be diagnosed after graft biopsy. If the result is lower than 0.650, it may be predicted that acute rejection will not be diagnosed after graft biopsy.

Another aspect of the present invention provides a composition for diagnosing acute rejection, the composition including an agent capable of measuring the expression levels of one or more miRNAs selected from the group consisting of miR-4488, miR-4532, miR-146a-5p, miR-21-5p, miR-373-3p, miR-31-5p, miR-223-3p, miR-210-3p, and a combination thereof.

As used herein, the term "agent capable of measuring the expression levels of miRNAs" refers to an agent capable of recognizing the miRNAs by specifically binding thereto or amplifying the miRNAs. Specific examples thereof may be primers or probes capable of specifically binding to the miRNAs, but are not limited thereto. Those skilled in the art will be able to select an appropriate agent depending on the purpose of the present invention.

The agent may be directly or indirectly labeled in order to measure the expression levels of the genes. Specifically, the label may include ligands, beads, radionuclides, enzymes, substrates, cofactors, inhibitors, fluorescent materials, chemiluminescent materials, magnetic particles, hapten, dyes, etc., but is not limited thereto. For specific example, the ligands may include biotin, avidin, streptoavidin, etc., the enzymes may include luciferase, peroxidase, beta galactosidase, etc., and the fluorescent materials may include fluorescein, coumarin, rhodamine, phycoerythrin, sulforhodamine acid chloride (Texas red), etc., but are not limited thereto. Most of the known labels may be used as such detectable labels, and those skilled in the art will be able to select an appropriate label depending on the purpose of the present invention.

The term 'primer', which is a short base sequence having a free 3'-hydroxyl group, refers to a short sequence that forms a base pair with a complementary template and serves as a starting point to copy the template strand. In the present invention, the primer used for miRNA amplification may be a single-stranded oligonucleotide capable of acting as a point of initiation of template-directed DNA synthesis under appropriate conditions (e.g., four different nucleoside triphosphates and an agent for polymerization, such as DNA or RNA polymerase or reverse transcriptase) in an appropriate buffer and at a suitable temperature. The appropriate length of the primer depends on the intended use. The primer sequence need not to be fully complementary to a polynucleotide of miRNA of the gene or a complementary polynucleotide thereof, and any primer sequence may be used as long as it is complementary enough to hybridize.

The term 'probe' refers to a labeled nucleic acid fragment or peptide capable of specifically binding with the miRNA. For specific example, the probe may be prepared in the form of an oligonucleotide probe, a single stranded DNA probe, a double stranded DNA probe, an RNA probe, an oligonucleotide peptide probe, a polypeptide probe, etc.

As used herein, the term "diagnosis" encompasses determining the susceptibility of a subject to a particular disease or disorder, determining whether the subject has a particular disease or disorder at present, determining the prognosis of the subject having a particular disease or disorder, or therametrics (e.g., monitoring the status of the subject in order to provide information for therapeutic effects).

In the present invention, the diagnosis may be interpreted as confirming whether or not a kidney transplant patient has the likelihood of the onset of acute rejection or has developed acute rejection.

Still another aspect of the present invention provides a kit for diagnosing acute rejection, the kit including the composition.

A quantitative system included in the diagnostic kit of the present invention may be to measure the expression levels of 8 kinds of miRNAs. For specific example, the quantitative system may be an RT-PCR kit, but is not limited thereto, as long as it is able to measure the expression levels of miRNAs.

In this regard, the RT-PCR kit may be a kit including essential elements needed to perform RT-PCR. For example, the RT-PCR kit may include, in addition to primers specific to each gene, a test tube or another appropriate container, a reaction buffer (varying pH and magnesium concentration), deoxynucleotides (dNTPs), dideoxynucleotides (ddNTPs), enzymes such as Taq-polymerase and reverse transcriptase, a DNase or RNAse inhibitor, DEPC-water, sterile water, etc. The RT-PCR kit may also include a pair of primers specific to a gene used as a quantitative control.

Still another aspect of the present invention provides a method of predicting or identifying the onset of acute rejection in a kidney transplant patient, and treating the same.

Specifically, the method of treating acute rejection in a kidney transplant patient of the present invention may include the steps of:

(a) obtaining a sample isolated from an individual suspected of developing acute kidney transplant rejection;

(b) quantitatively analyzing expression levels of one or more miRNAs selected from the group consisting of miR-4488, miR-4532, miR-146a-5p, miR-21-5p, miR-373-3p, miR-31-5p, miR-223-3p, miR-210-3p, and a combination thereof in the obtained sample;

(c) correlating the quantitatively analyzed miRNA expression levels with the onset of acute kidney transplant rejection to predict or identify the onset of acute kidney transplant rejection; and (d) treating acute rejection in the individual whose the onset of acute kidney transplant rejection is predicted or identified.

The steps (a) to (c) are the same as described above.

Hereinafter, the step (d) will be described in detail.

In the step (c), a step of specifically identifying the onset of acute rejection in the individual who is predicted to develop acute rejection after kidney transplantation may be further performed.

The step of specifically identifying the onset of acute rejection may be performed by a rejection test method known in the art, for example, by urine output measurement, quantitative analysis of a serum creatinine level, ultrasonography, kidney biopsy, etc., but is not limited thereto.

A known acute rejection therapy is performed for the individual who is predicted or identified to develop acute rejection after kidney transplantation, thereby treating acute rejection.

The known acute rejection therapy may include steroid pulse therapy, anti-T cell antibody (anti-thymocyte globulin, ATG) therapy, high-dose treatment or modulation of an immunosuppressive agent, etc.

Generally, when acute rejection is predicted or identified, a steroid pulse therapy is performed. According to the known report, a therapeutic response rate of steroid pulse therapy is 80% to 85% and a relapse rate thereof is 33%.

If acute rejection is not treated by the steroid pulse therapy, anti-T cell antibody therapy is used. It is known that a therapeutic response rate thereof is 65% to 100%, and a relapse rate thereof is 25%.

Lastly, the high-dose treatment or modulation of an immunosuppressive agent is a method of preventing recurrent rejection, and an immunosuppressive agent such as steroids, cyclosporine, tacrolimus, mycophenolate, etc. may be used by increasing or modulating the dose thereof.

Hereinafter, the present invention will be described in more detail with reference to Examples. However, these Examples are for illustrative purposes only, and the scope of the present invention is not intended to be limited by these Examples.

Example 1: Identification of Biomarker Candidates for Diagnosing Kidney Transplant Rejection Using Bioinformatics Technique Urinary exosome-derived miRNA biomarker candidates for diagnosing kidney transplant rejection were identified using two methods based on bioinformatics techniques.

Example 1-1: Method of Using Database

First, miRNA target databases were downloaded from miRTarBase, TargetScan, and microRNA. It is known that the microRNA and TargetScan databases include predicted targets by a calculation method, and the miRTarBase database includes only experimentally validated targets. The databases were used to select target pairs having the highest score from a plurality of target pairs consisting of one miRNA and a plurality of genes, and 1,110,357 target pairs with respect to a total of 1,802 miRNAs were primary selected.

The primary selected target pairs were integrated to display the score of each miRNA target database. If target pairs were not in the corresponding miRNA target database, their score was set to 0, and target pairs included in both microRNA and TargetScan or included in miRTarBase were selected as final targets. 405,092 target pairs with respect to 1.760 miRNAs were secondary selected.

Genes included in the secondary selected target pairs were subjected to meta-analysis, and 806 major genes satisfying FDR<0.1 and FC>1.25 were tertiary selected. However, genes associated immune traits, such as HLA, immunoglobulin, etc., and hypothetical predicted genes were excluded.

In order to select genes corresponding to key genes involved in kidney transplant rejection from the tertiary selected genes, statistical analysis was performed. Roughly, a p-value and an odd ratio were calculated using the Fisher test, and the p-value was converted to a false discovery rate for multiple hypothesis testing. As a result, biomarker candidates with FDR<0.05 were identified (Table 1).

TABLE 1

| | Biomarker candidates | | | | | | |
|---|---|---|---|---|---|---|---|
| miRNA | N1 | N2 | N3 | N4 | P | Odd | FDR |
| mir-335 | 177 | 629 | 2573 | 17254 | 4.742678e−12 | 1.887040 | 8.347113e−09 |
| mir-124 | 88 | 718 | 1312 | 18515 | 6.228241e−06 | 1.729549 | 5.480852e−03 |
| mir-146a | 34 | 772 | 857 | 19470 | 1.235519e−05 | 2.401762 | 7.248377e−03 |
| mir-221 | 54 | 752 | 706 | 19121 | 1.733904e−05 | 1.944757 | 7.629180e−03 |
| mir-30a | 98 | 708 | 1597 | 18230 | 5.357803e−05 | 1.580011 | 1.885947e−02 |
| mir-7107 | 17 | 789 | 133 | 19694 | 8.118225e−05 | 3.190130 | 2.381346e−02 |

Example 1-2: Method of Using GSEA (Gene Set Enrichment Analysis)

miRNA GSEA (Gene set enrichment analysis) was performed using MSigDB miRNA gene sets (C3) for the four rejection mRNA data sets (GSE9489, GSE25902, GSE36059, and GSE50058) which were used in the meta-analysis of Example 1-1.

As a result, gene sets with FDR<0.1 were identified only in GSE25902, thereby identifying biomarker candidates showing high levels of NES among miRNAs (FDR<0.1) of which expression levels were found to be significantly high in GSE25902 (Table 2).

TABLE 2

| Biomarker candidates | | | | | | |
|---|---|---|---|---|---|---|
| miRNA | size | ES | NES | NOM p-val | FDR q-val | PWER p-val |
| MIR-186 | 230 | −0.4363128 | −1.67860 | 0.005952381 | 0.09981297 | 0.203 |
| MIR-324-3P | 81 | −0.4077800 | −1.67639 | 0.020790020 | 0.09264262 | 0.207 |
| MIR-518A-2 | 178 | −0.4638104 | −1.67244 | 0.014170040 | 0.09074996 | 0.214 |
| MIR-154, MIR-487 | 55 | −0.5133539 | −1.67019 | 0.032653060 | 0.08558552 | 0.216 |
| MIR-373 | 197 | −0.4090277 | −1.66033 | 0.003976143 | 0.08820397 | 0.230 |
| MIR-31 | 61 | −0.4981911 | −1.65483 | 0.015936255 | 0.08674568 | 0.238 |

5 miRNAs with low FDR values (miR-335, miR-124, miR-146a-5p, miR-21-5p, and miR-30a) among the biomarker candidates identified in Example 1-1 and clearly identified 5 miRNAs (miR-186, miR-324-3P, miR-518A-2, miR-373-3p, and miR-31-5p) among the biomarker candidates identified in Example 1-2 were determined as biomarker candidates based on bioinformatics techniques.

Example 2: Selection of Patients 758 samples, including peripheral blood mononuclear cells, plasma, serum, blood RNA, urine supernatant, and urine RNA, etc., were collected from 615 kidney allograft patients who received kidney transplantation in 6 centers (Kyung Hee University Hospital at Gangdong, Kyungpook National University Hospital, Kyung Hee Medical Center. Samsung Seoul Hospital, Seoul St. Mary's Hospital, Inje University Paik Hospital) from September 2013 to March 2017, respectively, and subject patients for the study were selected through ARTKT-1 (assessment of immunologic risk and tolerance in kidney transplantation).

Among the selected patient samples, 108 samples of a normal control group (a normal renal function and pathology group (NP) and a long-term good survival normal renal function group (LGS), n=48) and an acute rejection group (an acute T cell-mediated rejection group (acute TCMR) and an acute antibody-mediated rejection group (acute ABMR), n=60)) were used in developing urinary exosomal miRNA biomarkers for rejection (Table 3).

TABLE 3

| Samples for biomarker development | | | | | |
|---|---|---|---|---|---|
| | NP | acute TCMR | acute ABMR | LGS | p value |
| Number of patients (n) | 19 | 40 | 20 | 29 | — |
| Age (years) | 47.3 ± 9.8 | 47.6 ± 12.0 | 47.5 ± 9.1 | 57.4 ± 9.5 | 0.001 |
| Sex (male, %) | 11 (57.9) | 25 (62.5) | 14 (70.0) | 8 (27.6) | 0.009 |
| Days after transplantation (days) | 190 ± 223 | 385 ± 510 | 833 ± 1485 | 5907 ± 2084 | <0.001 |
| ABO incompatible KT (n, %) | 2 (10.5) | 8 (20.0) | 9 (45.0) | 0 (0.0) | 0.003 |
| HLA mismatching (n) | 3.5 ± 2.0 | 3.5 ± 1.5 | 3.9 ± 1.4 | 2.2 ± 2.4 | 0.005 |
| Indication for renal biopsy | | | | | |
| Protocol biopsy (n, %) | 18 (94.7) | 11 (27.5) | 3 (15.0) | 0 (0) | |
| Elevated creatinine levels (n, %) | 1 (5.3) | 27 (67.5) | 15 (75.0) | 0 (0) | <0.001 |
| Proteinuria (n, %) | 0 (0) | 2 (5.0) | 2 (10.0) | 0 (0) | |
| Not done (n, %) | 0 (0) | 0 (0) | 0 (0) | 29 (100) | |
| eGFR (ml/min) | 71.1 ± 15.6 | 37.2 ± 21.8 | 37.4 ± 18.0 | 74.1 ± 12.5 | <0.001 |
| Urine PCR (mg/g) | 50 ± 43 | 801 ± 1228 | 1587 ± 2014 | 224 ± 360 | 0.003 |
| Maintenance immunosuppression | | | | | |
| Steroid (n, %) | 17 (89.5) | 34 (85.0) | 18 (90.0) | 13 (44.8) | <0.001 |
| Tacrolimus (n, %) | 19 (100) | 31 (77.5) | 13 (65.0) | 10 (34.5) | <0.001 |
| Cyclosporine (n, %) | 0 (0) | 6 (15.0) | 7 (35.0) | 15 (51.7) | <0.001 |
| Mycophenolate mofetil (n, %) | 19 (100) | 26 (65.0) | 19 (95.0) | 10 (34.5) | <0.001 |

TABLE 3-continued

| | Samples for biomarker development | | | | |
|---|---|---|---|---|---|
| | NP | acute TCMR | acute ABMR | LGS | p value |
| mTOR inhibitor (n, %) | 2 (10.5) | 4 (10.0) | 0 (0) | 3 (10.3) | 0.535 |
| | | Donor information | | | |
| Age (years) | 40.5 ± 15.1 | 48.6 ± 11.3 | 43.4 ± 10.5 | 32.9 ± 10.1 | <0.001 |
| Sex (Male, %) | 12 (63.2) | 25 (62.5) | 9 (45.0) | 16 (55.2) | 0.534 |
| Deceased donor (n, %) | 8 (42.1) | 22 (55.0) | 3 (15.0) | 4 (13.8) | <0.001 |

Among the remaining 650 samples, 260 samples obtained from patients of the normal renal function group (NP), the acute rejection group (acute TCMR/acute ABMR), the long-term good survival normal renal function group (LGS), BK virus nephropathy (BKVN), other diseases (OGIs), etc. were used to validate the developed urinary exosomal miRNA biomarkers for rejection (Table 4).

TABLE 4

| | Samples for biomarker development | | | | | | | |
|---|---|---|---|---|---|---|---|---|
| | NP | acute TCMR | acute ABMR | LGS | chronic ABMR | BKVAN | OGI | p value |
| Number of patients (n) | 50 | 50 | 30 | 30 | 20 | 20 | 60 | — |
| Age (years) | 45.6 ± 13.4 | 46.6 ± 12.4 | 48.5 ± 9.0 | 50.9 ± 8.5 | 47.9 ± 12.3 | 45.9 ± 15.8 | 47.9 ± 12.2 | 0.591 |
| Sex (male, %) | 27 (54.0) | 38 (76.0) | 19 (63.3) | 15 (50.0) | 12 (60.0) | 16 (80.0) | 44 (73.3) | 0.053 |
| Days after transplantation (days) | 164 ± 370 | 689 ± 808 | 2169 ± 1758 | 5324 ± 1511 | 2969 ± 1633 | 292 ± 292 | 1226 ± 1844 | <0.001 |
| ABO incompatible KT (n, %) | 4 (8.0) | 5 (10.0) | 2 (6.7) | 1 (3.3) | 1 (5.0) | 3 (15.0) | 3 (5.0) | 0.659 |
| HLA mismatching (n) | 3.1 ± 1.5 | 3.4 ± 1.6 | 3.5 ± 1.5 | 3.1 ± 1.5 | 3.1 ± 1.4 | 3.4 ± 1.8 | 3.5 ± 1.9 | 0.933 |
| | | | | Indication for renal biopsy | | | | |
| Protocol biopsy (n, %) | 40 (80.0) | 6 (12.0) | 0 (0) | 0 (0) | 0 (0) | 0 (0) | 17 (28.3) | |
| Elevated creatinine levels (n, %) | 10 (20.0) | 42 (84.0) | 28 (93.3) | 0 (0) | 15 (75.0) | 20 (100) | 37 (61.7) | <0.001 |
| Proteinuria (n, %) | 0 (0) | 2 (4.0) | 2 (6.7) | 0 (0) | 5 (25.0) | 0 (0) | 6 (10.0) | |
| Not done (n, %) | 0 (0) | 0 (0) | 0 (0) | 30 (100) | | | | |
| eGFR (ml/min) | 78.9 ± 24.4 | 35.0 ± 13.9 | 33.9 ± 14.8 | 79.0 ± 20.9 | 32.3 ± 18.3 | 37.9 ± 14.1 | 40.1 ± 16.7 | <0.001 |
| Urine PCR (mg/g) | 228 ± 423 | 984 ± 1576 | 2161 ± 2380 | 243 ± 241 | 2112 ± 1901 | 269 ± 170 | 1615 ± 2701 | <0.001 |
| | | | | Maintenance immunosuppression | | | | |
| Steroid (n, %) | 49 (98.0) | 44 (88.0) | 29 (96.7) | 21 (70.0) | 16 (80.0) | 19 (95.0) | 55 (91.7) | 0.601 |
| Tacrolimus (n, %) | 49 (98.0) | 40 (80.0) | 24 (80.0) | 17 (56.7) | 15 (75.0) | 19 (95.0) | 51 (95.0) | 0.619 |
| Cyclosporine (n, %) | 0 (0) | 6 (12.0) | 3 (10.0) | 11 (36.7) | 4 (20.0) | 0 (0) | 7 (11.7) | 0.379 |
| Mycophenolate mofetil (n, %) | 48 (96.0) | 43 (86.0) | 27 (90.0) | 23 (76.7) | 14 (70.0) | 13 (65.0) | 51 (85.0) | 0.014 |
| mTOR inhibitor (n, %) | 3 (6.0) | 2 (4.0) | 3 (10.0) | 2 (6.7) | 2 (10.0) | 2 (10.0) | 3 (5.0) | 0.896 |
| | | | | Donor information | | | | |
| Age (years) | 45.6 ± 12.9 | 49.6 ± 11.6 | 51.3 ± 12.9 | 35.0 ± 10.7 | 45.1 ± 13.7 | 52.5 ± 8.7 | 48.2 ± 13.4 | <0.001 |
| Sex (Male, %) | 29 (58.0) | 25 (50.0) | 13 (43.3) | 15 (50.0) | 10 (50.0) | 9 (45.0) | 32 (53.3) | 0.906 |
| Deceased donor (n, %) | 16 (32.0) | 22 (44.0) | 9 (30.0) | 4 (13.3) | 8 (40.0) | 8 (40.0) | 27 (45.0) | 0.081 |

As the urine supernatants, supernatants obtained by centrifuging the urine samples obtained from the patients at room temperature and 2,000 g for 20 minutes were used, and the urinary RNAs were obtained by applying 1 ml of the urine supernatant to an exoRNeasy serum/plasma midi kit available from Qiagen (Table 5). Quantitative and qualitative analysis of the obtained RNAs were performed using a Nanodrop ND-2000 UV spectrophotometer (Thermo Scientific). Each sample thus obtained was stored at −80° C.

TABLE 5

Total amount and purity of urinary RNA

|  | Samples for development | Samples for validation | P value |
|---|---|---|---|
| Total amount of RNA | 0.391 ± 0.136 | 0.294 ± 0.127 | <0.0001 |
| Purity of RNA | 1.49 ± 0.189 | 1.46 ± 0.082 | 0.1285 |

The average amount of urine RNA was about 320 ng and its purity was about 1.47. The amount of nucleic acid obtained from 1 ml of urine was low, which was a limitation in various experimental methods or high-throughput analysis. However, a recent nanostring method, which is a method of attaching a barcode of a single transcript by a hybridization method, unlike the existing transcriptome analysis methods (enzymes or library), has been developed to enable absolute count analysis even with a small amount of nucleic acid. Therefore, the present experimenters employed the nanostring method capable of identifying miRNA with a small amount of nucleic acid.

Example 3: miRNA Analysis Using Nanostring nCounter System miRNAs were analyzed by applying each 60 ng of urinary RNA samples included in 108 samples for biomarker development to Human V3 panel with 798 unique miRNA barcodes of nCounter system. The normal groups (NP+LGS; STA) and the rejection groups (acute TCMR+acute ABMR; AR) were compared by differential expression gene analysis which is a statistical method, and normalization of the urinary RNA samples was performed with a nSolver program using a positive control and five housekeeping genes (Ribosomal protein lateral stalk subunit P0, RPLP0; beta-actin, ACTB; beta-2-microglobulin, B2M; glyceraldehyde 3-phosphate dehydrogenase, GAPDH; ribosomal protein L19, RPL19). As a result, a total of 14 miRNAs with a fold change of 2 or more and a p value of 0.05 or less were identified (Table 6).

TABLE 6

Biomarker candidates identified through Nanostring nCounter system

| No. | Gene Name | Fold change (AR vs STA) | p-value |
|---|---|---|---|
| 1 | hsa-miR-1268a | −2.22 | 1.38E−05 |
| 2 | hsa-miR-1305 | −2.76 | 6.35E−05 |
| 3 | hsa-miR-187-3p | −2.55 | 2.93E−06 |
| 4 | hsa-miR-1915-3p | −8.79 | 0.00E+00 |
| 5 | hsa-miR-3158-3p | −4.99 | 3.00E−08 |
| 6 | hsa-miR-3185 | −2.03 | 1.74E−04 |
| 7 | hsa-miR-3195 | −4.39 | 0.00E+00 |
| 8 | hsa-miR-320e | −3 | 2.66E−04 |
| 9 | hsa-miR-4488 | −5.39 | 0.00E+00 |
| 10 | hsa-miR-4516 | −5.09 | 1.13E−06 |
| 11 | hsa-miR-4532 | −12.47 | 0.00E+00 |
| 12 | hsa-miR-489-3p | −6.1 | 0.00E+00 |
| 13 | hsa-miR-675 | −3.45 | 1.04E−06 |
| 14 | hsa-miR-197-5p | 2.17 | 7.09E−04 |

As shown in Table 6, among 14 miRNAs, only miR-197-5p was increased in the rejection groups, as compared with the normal groups, and the remaining 13 miRNAs were decreased in the rejection groups.

Example 4: Analysis of miRNA Expression Levels

Expression levels of miRNAs included in urinary RNA samples were analyzed by real-time PCR analysis using TaqMan Advanced miRNA assays (Applied Biosystems, ABI).

Briefly, each 2 ul of urinary RNAs obtained from 108 samples for biomarker development which were determined in Example 2 was applied to a TaqMan Advanced miRNA cDNA synthesis kit to synthesize each cDNA. 5 ul of the synthesized cDNA was applied to PCR with universal primers and a master mix to amplify the cDNA level. To the amplified cDNA, 10×TE buffer was added and diluted, and 5 ul of the diluted cDNA, 10 ul of TaqMan Fast Advanced Master Mix, 1 ul of miRNA primer (Table 7), and 4 ul of RNase-free water were mixed with each other to perform ABI stepOnePlus real-time PCR system. In this regard, the biomarker candidates to be amplified were a total of 26 candidates including 10 biomarker candidates identified using the bioinformatics techniques in Example 1, 11 biomarker candidates identified using the Nanostring nCounter system in Example 3 (among 14 biomarker candidates, miR-1268a, miR-1305, and miR-3195 were excluded due to failure to obtain primers and probes), and 5 biomarker candidates identified through literature review (miR-142-5p, miR-142-3p, miR-155-5p, miR-223-3p, and miR-210-3p), and PCR thermal cycling conditions are as follows: 40 cycles of at 95° C. for 20 sec, at 95° C. for 1 sec. and at 60° C. for 20 sec. To calculate the miRNA expression level from the obtained amplification product, a comparative threshold cycle method which is a method of normalizing with Ct values of human universal reference miRNA and miR-16-5p was used (FIGS. 1A to 1C). In this regard, miR-16-5p was used as an internal control, and 6 biomarker candidates (miR-1915-3p, miR-3158-3p, miR-197-5p, miR-518a-2, miR-142-5p, and miR-142-3p) were excluded, because they were not detected in 90% or more of test samples, and the results of analyzing only the remaining 20 biomarker candidates are illustrated.

TABLE 7

Primers used in mRNA analysis

| No. | Gene Name | Assay ID | Brand |
|---|---|---|---|
| 1 | hsa-miR-197-5p | 478748_mir | ABI |
| 2 | hsa-miR-187-3p | 477941_mir | ABI |
| 3 | hsa-miR-1915-3p | 478740_mir | ABI |
| 4 | hsa-miR-3158-3p | 479643_mir | ABI |
| 5 | hsa-miR-3185 | 478018_mir | ABI |
| 6 | hsa-miR-320e | 478022_mir | ABI |

TABLE 7-continued

Primers used in mRNA analysis

| No. | Gene Name | Assay ID | Brand |
|---|---|---|---|
| 7 | hsa-miR-4488 | 478906_mir | ABI |
| 8 | hsa-miR-4516 | 478303_mir | ABI |
| 9 | hsa-miR-4532 | 480831_mir | ABI |
| 10 | hsa-miR-489-3p | 478130_mir | ABI |
| 11 | hsa-miR-575 | 479056_mir | ABI |
| 12 | hsa-miR-124-3p | 477879_mir | ABI |
| 13 | hsa-miR-146a-5p | 478399_mir | ABI |
| 14 | hsa-miR-21-5p | 477975_mir | ABI |
| 15 | hsa-miR-30a-3p | 478273_mir | ABI |
| 16 | hsa-miR-335-5p | 478324_mir | ABI |
| 17 | hsa-miR-186-5p | 477940_mir | ABI |
| 18 | hsa-miR-324-3p | 478023_mir | ABI |
| 19 | hsa-miR-518a-5p | 479249_mir | ABI |
| 20 | hsa-miR-373-3p | 478363_mir | ABI |
| 21 | hsa-miR-31-5p | 478015_mir | ABI |
| 22 | hsa-miR-142-5p | 477911_mir | ABI |
| 23 | hsa-miR-142-3p | 477910_mir | ABI |
| 24 | hsa-miR-155-5p | 477927_mir | ABI |
| 25 | hsa-miR-223-3p | 477983_mir | ABI |
| 26 | hsa-miR-210-3p | 477970_mir | ABI |
| 27 | hsa-miR-16-5p | 477860_mir | ABI |

FIG. 1A shows graphs of the results of real-time PCR system for analyzing 8 biomarker candidates, except for undetected 3 biomarker candidates, among 11 biomarker candidates identified using the Nanostring nCounter system, FIG. 1B shows graphs of the results of real-time PCR system for analyzing 9 biomarker candidates, except for undetected 1 biomarker candidate, among 10 biomarker candidates identified using the bioinformatics techniques, and FIG. 1C shows graphs of the results of real-time PCR system for analyzing 3 biomarker candidates, except for undetected 2 biomarker candidate, among 5 biomarker candidates identified through literature review.

As shown in FIGS. 1A to 1C, the real-time PCR analysis results of 26 kinds of miRNAs showed that 10 kinds of miRNAs (miR-4488, miR-4532, miR-146a-5p, miR-21-5p, miR-373-3p, miR-31-5p, miR-223-3p, miR-210-3p, miR-324-3p, and miR155-5p) were identified as statistically significant miRNAs of the normal groups and rejection groups. Among them, 2 kinds of miRNAs (miR-324-3p and miR155-5p) showed a problem of very low frequency, because they were partially detected only in about 20% samples of the total samples.

Accordingly, among the 10 kinds of miRNAs, a total of 8 kinds of miRNAs (miR-4488, miR-4532, miR-146a-5p, miR-21-5p, miR-373-3p, miR-31-5p, miR-223-3p, and miR-210-3p), except for 2 kinds of miRNAs showing the low frequency, were finally selected as miRNA biomarkers for diagnosing kidney transplant rejection.

Example 5: Statistical Analysis

One-way analysis was performed for 8 kinds of miRNAs finally selected in Example 4 in order to compare means of patient characteristics. To compare urinary transcriptome expression levels between the acute rejection groups (AR) and the normal groups (stable graft function; STA) in the training set, a non-parametric Mann-Whitney test was used. Further, to compare mRNA expression between 4 clinical groups in the validation set, a non-parametric Kruskal-Wallis test was used.

To diagnose and predict acute rejection, the area under ROC (receiver operating characteristic) curve was analyzed by fitting a logistic regression model (FIG. 2). Furthermore, to provide high sensitivity and specificity, appropriate cutoff scores were determined at each measurement value. $p<0.05$ was considered statistically significant.

FIG. 2 shows graphs of the results of analyzing ROC curves of 8 kinds of miRNAs (miR-4488, miR-4532, miR-146a-5p, miR-21-5p, miR-373-3p, miR-31-5p, miR-223-3p, and miR-210-3p).

As shown in FIG. 2, 8 kinds of miRNAs showed AUC values from 0.614 to 0.732, respectively. A higher AUC value indicates a greater ability to distinguish the rejection patients from the normal group. 8 kinds of miRNAs, miR-31-5p, miR-21-5p, miR-223-3p, miR-4532, miR-373-3p, miR-4488, miR-210-3p, and miR-146a-5p, were ranked in descending order of the ability to distinguish rejection (AUC 0.732, 0.697, 0.679 0.676, 0.659, 0.638, 0.626, and 0.614, respectively).

Example 6: Development of Diagnostic/Predictive Models for Rejection 8 kinds of miRNAs finally selected in Example 4 were found not to have excellent ability to distinguish rejection, individually. Therefore, diagnostic/predictive models for rejection were developed through a statistical method.

A first model was developed using all 8 kinds of miRNAs by logistic regression:

$$\text{i) } \ln\left(\frac{p}{1-p}\right) = -1.284 + (0.267 \times miR4488) + (-1.361 \times miR4532) +$$
$$(1.544 \times miR21) + (0.015 \times miR223) + (1 \times miR31) +$$
$$(-0.497 \times miR146a) + (0.3 \times miR373) + (0.146 \times miR210)$$

A second model was developed using 3 kinds of miRNAs (miR-21-5p, miR-31-5p, and miR-4532) by FSS (forward stepwise selection):

$$\text{ii) } \ln\left(\frac{p}{1-p}\right) =$$
$$-1.158 + (-1.103 \times miR4532) + (1.2 \times miR21) + (1.16 \times miR31)$$

The two kinds of models developed above were used to predict rejection in 108 samples for biomarker development (FIGS. 3A and 3B).

FIG. 3A is a graph showing the results of predicting rejection in 108 samples for biomarker development using the first model.

As shown in FIG. 3A, AUC was 0.868 (95% Confidence Interval (CI), 802-934), indicating that the samples showing rejection may be clearly distinguished from the normal group.

FIG. 3B is a graph showing the results of predicting rejection in 108 samples for biomarker development using the second model.

As shown in FIG. 3B, AUC was 0.859 (95% CI, 792-927), also indicating that the samples showing rejection may be clearly distinguished from the normal group.

As shown in FIGS. 3A and 3B, the two models developed above clearly distinguished the samples showing rejection from the normal group, and there was no difference in the ability to distinguish rejection between the two models.

Example 7: Validation of Diagnostic/Predictive Models for Rejection

Example 7-1: Real-Time PCR Analysis in Samples for Biomarker Validation

Real-time PCR analysis of 8 kinds of miRNAs identified in Example 4 was performed in 260 samples for biomarker validation which were determined in Example 2 (FIG. 4A). In this regard, 260 samples for biomarker validation included a normal pathology group (NP/LGS, n=80), a rejection group (ACR/AMR, n=80), a chronic renal allograft dysfunction group (CAD, n=20), a BK virus nephropathy group (BKVN, n=20), and other transplant kidney injury group (n=60).

FIG. 4A shows graphs of the results of real-time PCR analysis of 8 kinds of miRNAs identified in Example 4 in 260 samples for biomarker validation.

As shown in FIG. 4A, among 8 kinds of miRNAs, 3 kinds of miRNAs including miR-21-5p, miR-4488, and miR-4532 showed statistically significant results in the samples for biomarker validation.

Example 7-2: Analysis of Diagnostic/Predictive Models for Rejection Using Samples for Biomarker Validation 260 samples for biomarker validation which were determined in Example 2 were analyzed using the two kinds of diagnostic/predictive models for rejection which were developed in Example 6 (FIGS. 4B and 4C).

FIG. 4B is a graph showing the results of predicting rejection in 260 samples for biomarker validation using the first model.

As shown in FIG. 4B, AUC was 0.766 (95% CI, 694-839), sensitivity was 67.5%, specificity was 69.7%, and a cut-off point thereof was 0.572.

FIG. 4C is a graph showing the results of predicting rejection in 260 samples for biomarker validation using the second model.

As shown in FIG. 4C, AUC was 0.779 (95% CI, 708-850), sensitivity was 53.8%, specificity was 80.3%, and a cut-off point thereof was 0.650.

Based on the cut-off points of FIGS. 4B and 4C, the second model was more effective for the samples for biomarker validation than the first model.

Taken together, the above-described results of Examples suggest that 8 kinds of miRNAs provided in the present invention may be used as markers for diagnosing or predicting rejection according to kidney transplantation.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

Effect of the Invention

Since miR-4488, miR-4532, miR-146a-5p, miR-21-5p, miR-373-3p, miR-31-5p, miR-223-3p, and miR-210-3p according to the present invention exist in high levels in the urine of a patient with acute kidney transplant rejection, they may be used to easily diagnose the onset of acute kidney transplant rejection, thereby being used in the effective treatment of acute rejection after kidney transplantation.

What is claimed is:

1. A method of treating acute rejection of a kidney transplant, the method comprising the steps of:
   (a) obtaining a urine sample isolated from an individual suspected of developing acute kidney transplant rejection;
   (b) quantitatively analyzing expression levels of miRNAs miR-4532, miR-21-5p, and miR-31-5p in the obtained urine sample;
   (c) correlating the quantitatively analyzed miRNA expression levels with the onset of acute kidney transplant rejection by applying a regression model of Equation 2:

$$\ln\left(\frac{p}{1-p}\right) = -1.158 + (-1.103 \times miR4532) + (1.2 \times miR21) + (1.16 \times miR31)$$

in which
   miR4532 represents the expression level of miR-4532,
   miR21 represents the expression level of miR-21-5p, and
   miR31 represents the expression level of miR-31-5p;
   (d) predicting that the individual has or will develop acute rejection when the result of Equation 2 is greater than 0.650; and
   (e) treating the individual, wherein the treating is performed by steroid pulse therapy, anti-T cell antibody therapy, or high-dose treatment or modulation of an immunosuppressive agent.

2. The method of claim 1, wherein the anti-T cell antibody therapy is performed by administering monoclonal or polyclonal antibody against T cells.

3. The method of claim 1, wherein the high-dose treatment or modulation of an immunosuppressive agent is performed using steroids, cyclosporine, tacrolimus, or mycophenolate.

4. A method of treating acute rejection of a kidney transplant, the method comprising the steps of:
   (a) obtaining a urine sample isolated from an individual suspected of developing acute kidney transplant rejection;
   (b) quantitatively analyzing expression levels of miRNAs miR-4488, miR-4532, miR-146a-5p, miR-21-5p, miR-373-3p, miR-31-5p, miR-223-3p, and miR-210-3p in the obtained urine sample;
   (c) correlating the quantitatively analyzed miRNA expression levels with the onset of acute kidney transplant rejection by applying a regression model of Equation 1:

$$\ln\left(\frac{p}{1-p}\right) = -1.284 + (0.267 \times miR4483) +$$
$$(-1.361 \times miR4532) + (1.544 \times miR21) + (0.015 \times miR223) +$$
$$(1 \times miR31) + (-0.497 \times miR146a) + (0.3 \times miR373) + (0.146 \times miR210)$$

in which
   miR4488 represents an expression level of miR-4488,
   miR4532 represents an expression level of miR-4532,
   miR21 represents an expression level of miR-21-5p,
   miR223 represents an expression level of miR-223-3p,
   miR31 represents an expression level of miR-31-5p,
   miR146a represents an expression level of miR-146a-5p, miR373 represents an expression level of miR-373-3p, and miR210 represents an expression level of miR-210-3p;

(d) predicting that the individual has or will develop acute rejection when the result of Equation 1 is greater than 0.572; and (e) treating the individual, wherein the treating is performed by steroid pulse therapy, anti-T cell antibody therapy, or high-dose treatment or modulation of an immunosuppressive agent.

5. The method of claim 4, wherein the anti-T cell antibody therapy is performed by administering monoclonal or polyclonal antibody against T cells.

6. The method of claim 4, wherein the high-dose treatment or modulation of an immunosuppressive agent is performed using steroids, cyclosporine, tacrolimus, or mycophenolate.

\* \* \* \* \*